United States Patent

Bantick

[11] Patent Number: 4,474,788
[45] Date of Patent: Oct. 2, 1984

[54] ANTI-SRSA QUINOLINE CARBOXYLIC ACID DERIVATIVES

[75] Inventor: John R. Bantick, Loughborough, England

[73] Assignee: Fisons plc, Ipswich, England

[21] Appl. No.: 438,163

[22] Filed: Nov. 1, 1982

[30] Foreign Application Priority Data

Nov. 12, 1982 [GB] United Kingdom ................. 8134186

[51] Int. Cl.³ .................... A61K 31/47; C07D 215/16
[52] U.S. Cl. .................................. 424/258; 546/153; 546/156
[58] Field of Search ................. 546/156, 153; 424/258

[56] References Cited

FOREIGN PATENT DOCUMENTS 2554772  6/1976  Netherlands ........................ 544/156

Primary Examiner—Paul M. Coughlan, Jr.
Assistant Examiner—Cecilia Shen
Attorney, Agent, or Firm—Marshall, O'Toole, Gerstein, Murray & Bicknell

[57] ABSTRACT

There are described compounds of formula I,

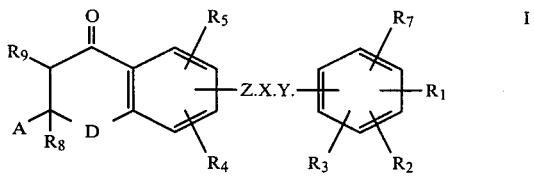

in which
$R_1$, $R_2$, $R_3$, $R_4$, $R_5$ and $R_7$, which may be the same or different, each represent hydrogen, hydroxy, alkyl C1 to 6, alkoxy C1 to 6, amino, acyl C2 to 6, acylamino C2 to 6, alkenyl C2 to 6, halogen, or alkoxy C1 to 6 substituted by phenyl, X is a hydrocarbon chain of 1 to 10 carbon atoms optionally substituted by a hydroxy group, A is —Q—COOH, Q is absent or represents a straight or branched alkylene, alkenylene or alkynylene group of up to and including 6 carbon atoms, $R_8$ and $R_9$, which may be the same or different, each represent hydrogen or alkyl C1 to 6 or together form a single bond, D, Y and Z, which may be th same or different, each represent sulphur, oxygen or —$NR_{10}$—, and $R_{10}$ is hydrogen or alkyl C1–C6, provided that
(i) when D, Z and Y are all oxygen, $R_8$ and $R_9$ do not together form a single bond,
(ii) when D is oxygen, $R_8$ and $R_9$ together form a single bond, X is $(CH_2)_5$, A is —COOH, one of Y and Z is sulphur and the other is oxygen, at least one of $R_1$, $R_2$, $R_3$, $R_4$, $R_5$ and $R_7$ is other than hydrogen, and pharmaceutically acceptable salts, esters and amides thereof.

There are also described processes to these compounds, and pharmaceutical, e.g. anti-allergic, compositions containing them.

9 Claims, No Drawings

ANTI-SRSA QUINOLINE CARBOXYLIC ACID DERIVATIVES

This invention relates to new compounds, methods for their preparation and compositions containing them.

According to our invention we provide a compound of formula I,

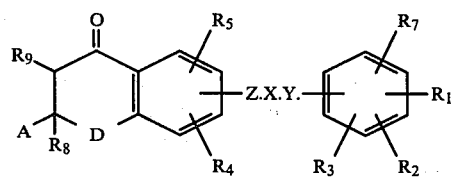

in which $R_1$, $R_2$, $R_3$, $R_4$, $R_5$ and $R_7$, which may be the same or different, each represent hydrogen, hydroxy, alkyl C1 to 6, alkoxy C1 to 6, amino, acyl C2 to 6, acylamino C2 to 6, alkenyl C2 to 6, halogen, or alkoxy C1 to 6 substituted by phenyl, X is a hydrocarbon chain of 1 to 10 carbon atoms optionally substituted by a hydroxy group, A is —Q—COOH, Q is absent or represents a straight or branched alkylene, alkenylene or alkynylene group of up to and including 6 carbon atoms, $R_8$ and $R_9$, which may be the same or different, each represent hydrogen or alkyl C1 to 6 or together form a single bond, D, Y and Z, which may be the same or different, each represent sulphur, oxygen or —$NR_{10}$—, and $R_{10}$ is hydrogen or alkyl C1–C6, provided that (i) when D, Z and Y are all oxygen, $R_8$ and $R_9$ do not together form a single bond, (ii) when D is oxygen, $R_8$ and $R_9$ together form a single bond, X is $(CH_2)_5$, A is —COOH, one of Y and Z is sulphur and the other is oxygen, at least one of $R_1$, $R_2$, $R_3$, $R_4$, $R_5$ and $R_7$ is other than hydrogen, and pharmaceutically acceptable salts, esters and amides thereof.

Where one or more of $R_1$, $R_2$, $R_3$, $R_4$, $R_5$ and $R_7$ represents alkyl or alkoxy, it is preferably of 1 to 4 carbon atoms and is desirably a straight chain alkyl or alkoxy group. Specific preferred alkyl groups are methyl, ethyl, n-propyl, n-butyl, and preferred alkoxy groups are the alkoxy equivalents of these, especially methoxy and ethoxy. Benzyloxy is a particularly preferred alkoxy group substituted by phenyl.

Preferably, at least one of $R_4$ and $R_5$ and, independently, at least one of $R_1$, $R_2$, $R_3$ and $R_7$ represents an alkyl group.

When one or more of $R_1$, $R_2$, $R_3$, $R_4$, $R_5$ and $R_7$ represents acyl or acylamino, the acyl moiety is desirably an alkanoyl moiety, especially of 2 to 4 carbon atoms. Acetyl and acetylamino are particularly preferred.

Desirably, at least one of $R_1$, $R_2$, $R_3$ and $R_7$ represents acyl.

Desirably, at least one of $R_1$, $R_2$, $R_3$ and $R_7$ represents hydroxy.

When one or more of $R_1$, $R_2$, $R_3$, $R_4$, $R_5$ and $R_7$ represents alkenyl it is preferably of 2 to 4 carbon atoms, and is especially vinyl or allyl.

When one or more of $R_1$, $R_2$, $R_3$, $R_4$, $R_5$ and $R_7$ represents halogen, it is preferably chlorine, bromine or iodine, chlorine and bromine being especially preferred.

At least one of $R_4$ and $R_5$ preferably represents hydrogen.

$R_4$ is preferably in the 8-position when it represents other than hydrogen.

$R_5$ is preferably in the 6-position when it represents other than hydrogen.

The group X is preferably of 3 to 7 carbon atoms, and may be straight or branched. It is preferably a straight chain alkylene group optionally substituted by a hydroxy group. Specific preferred groups which X may represent are 1,3-trimethylene, 2-hydroxy-1,3-trimethylene, and 1,5-pentamethylene.

Y and Z both preferably represent oxygen.

The group Q is preferably absent or is alkylene or alkenylene of 2 to 4 carbon atoms and is desirably a straight chain group, e.g. ethenylene, 1,2-dimethylene or 1,3-trimethylene.

We prefer $R_8$ and $R_9$ together to form a single bond, or both to represent hydrogen.

A preferred group of compounds of formula I comprises those wherein the —Z.X.Y— chain is bonded to the bicylcic ring system in the 6- or 7-position (particularly in the 7-position).

A particularly preferred group of compounds comprises those wherein $R_1$ represents hydrogen or alkanoyl of 2 to 4 carbon atoms, $R_2$ represents hydrogen, amino or hydroxy; $R_3$, $R_4$ and $R_5$ each represent hydrogen or alkyl of 1 to 4 carbon atoms, $R_7$ represents hydrogen or alkyl of 1 to 4 carbon atoms, X represents straight chain alkylene of 3 to 7 carbon atoms optionally substituted by a hydroxy group, both Y and Z represent oxygen, and Q is absent or represents a straight chain alkylene or alkenylene group of 2 to 6 carbon atoms, and the pharmaceutically acceptable salts thereof.

An especially preferred group of compounds comprises those wherein $R_1$ is in the 4-position with respect to Y, and represents hydrogen or alkanoyl of 2 to 4 carbon atoms, $R_2$ is in the 3-position with respect to Y and represents hydrogen, amino or hydroxy, $R_3$ is in the 2-position with respect to Y, and represents hydrogen, alkyl of 1 to 4 carbon atoms, or alkanoyl of 2 to 4 carbon atoms, $R_4$ is in the 8-position, and represents hydrogen or alkyl of 1 to 4 carbon atoms, $R_5$ is in the 6 position, and represents hydrogen or alkyl of 1 to 4 carbon atoms, $R_7$ is in the 6 position with respect to Y and represents hydrogen or alkyl 1 to 4 carbon atoms, Z is in the 7 position and represents oxygen, Y represents oxygen, X represents a straight chain alkylene of 3 to 5 carbon atoms optionally substituted by a hydroxy group, and Q represents a straight chain alkylene or alkenylene group of 2 to 4 carbon atoms, and the pharmaceutically acceptable salts thereof.

Pharmaceutically acceptable salts of the compounds of formula I include the alkali-metal and alkaline-earth metal salts, e.g. the potassium, lithium and calcium salts and, notably the sodium salt. Also included are salts with organic bases, e.g. optionally hydroxy-substituted alkylamines, e.g. methylamine and ethylamine, and bases containing both nitrogen and oxygen atoms; specifically salts with alkanolamines, e.g. tri- and diethanolamine; hydroxy-alkylalkylamines, e.g. tri-(hydroxymethyl)methylamine; 5 or 6 membered nitrogen containing heterocyclic rings, e.g. morpholine; N-alkylamino substituted sugars, e.g. N-methylglucamine; and amino acids, e.g. lysine, ornithine or arginine.

Esters within the scope of the invention include alkyl esters, especially of 1 to 6 carbon atoms, e.g. the methyl and ethyl esters. The amides may be, for example, unsubstituted or mono- or di- C1 to 6 alkyl or phenyl amides.

Specific preferred compounds of the invention are those of the Examples, 7-(3-[4-Acetyl-3-hydroxy-2-propylphenoxy]propyloxy-1-ethyl-1,4-dihydro-4-oxo-8-propylquinoline-2-carboxylic acid and 7-(3-[4-Acetyl-3-hydroxy-2-propylphenoxy]propoxy)-4-oxo-8-propyl-4H-1-benzothiapyran-2-propanoic acid.

According to our invention we also provide a process for the production of a compound of formula I, or a pharmaceutically acceptable salt, ester or amide thereof, which comprises:

(a) producing a free carboxylic acid of formula I by selective hydrolyses of a compound of formula II,

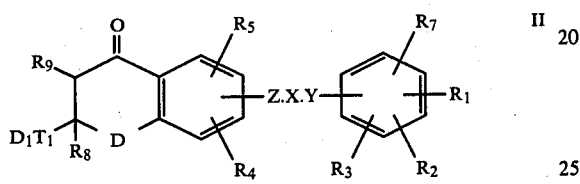

in which $R_1$, $R_2$, $R_3$, $R_4$, $R_5$, $R_7$, $R_8$, $R_9$, X, Y, Z and D are as defined above, $T_1$ represents a group Q as defined above, and $D_1$ represents a group hydrolysable to a carboxyl group, (b) producing a free carboxylic acid or ester of a compound of formula I in which A is T.CH=CH.COOH, where T is absent or represents C1-4 straight or branched alkylene, by reacting a compound of formula II, in which $T_1$ represents T, $D_1$ represents —CHO, and $R_1$, $R_2$, $R_3$, $R_4$, $R_5$, $R_7$, $R_8$, $R_9$, X, Y, Z and D are as defined above, (i) with a compound of formula HOOC—CH=P(R)$_3$ or of formula HOOC—CH$_2$—P(=O)(OR)$_2$ where R represents phenyl or alkyl of 1 to 6 carbon atoms, or an ester or salt of either thereof, or (ii) with malonic acid or an ester thereof and selectively hydrolysing and decarboxylating the product, (c) producing a compound of formula I in which Q represents a straight or branched alkylene group of 2 to 6 carbon atoms, by selective reduction of a compound of formula II, in which $T_1$ represents a straight or branched alkenylene or alkynylene group of up to and including 6 carbon atoms, $D_1$ represents a carboxy group or an ester, amide or salt thereof, and $R_1$, $R_2$, $R_3$, $R_4$, $R_5$, $R_7$, $R_8$, $R_9$, D, X, Y and Z are as defined above, (d) producing a compound of formula I in which A represents $T_2$—C≡C—COOH, where $T_2$ is absent or represents a straight or branched alkylene group of up to and including 4 carbon atoms, by subjecting to an elevated temperature a compound of formula II, in which $T_1$ represents a group $T_2$ as defined immediately above, $D_1$ represents —CO.C(COOH)=P(R)$_3$, where R is as defined above, or an ester thereof, and $R_1$, $R_2$, $R_3$, $R_4$, $R_5$, $R_7$, $R_8$, $R_9$, D, X, Y and Z are as defined above, (e) producing a salt of a compound of formula I, in which Q represents —C≡C—, by subjecting to the action of a base a compound of formula II where $T_1$ is absent and $D_1$ represents —C(OSO$_2$A$_1$)=C(COOR)$_2$, where R is as defined above and A$_1$ represents a C6-9 aryl moiety, (f) producing a pharmaceutically acceptable salt, ester or amide of a compound of formula I, by salifying, esterifying or amidating a compound of formula I or a suitable derivative thereof, (g) reacting a compound of the formula XX,

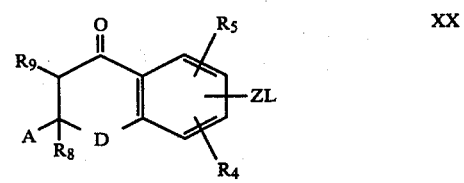

or a salt, ester or amide thereof, with a compound of the formula XXI,

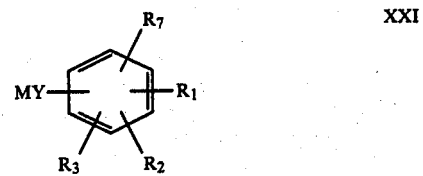

in which $R_1$, $R_2$, $R_3$, $R_4$, $R_5$, $R_7$, $R_8$, $R_9$, D, Z, Y and A are as defined above, and L and M represent the pair of groups (i) hydrogen or a reactive metal and (ii) a hydrocarbon chain of 1 to 10 carbon atoms carrying a leaving group or an epoxide group, (h) producing a compound of formula I in which $R_8$ and $R_9$ together form a single bond, by cyclising a compound of the formula XXX,

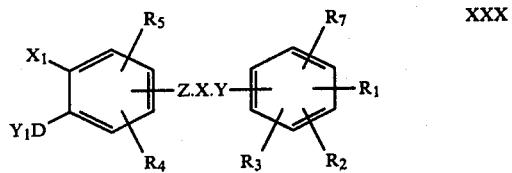

or a salt, ester or amide thereof, in which

D, $R_1$, $R_2$, $R_3$, $R_4$, $R_5$, $R_7$, Z, X and Y are as defined above, $X_1$ represents a group —COCHR$_9$COQ—COOH where Q and $R_9$ are as defined above, and $Y_1$ represents hydrogen or a displaceable protecting group, (i) producing a compound of formula I, or an ester thereof, by cyclising a compound of formula XXXI,

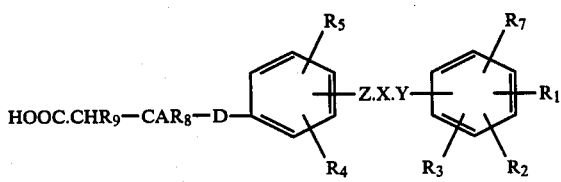

or an ester, or esters, thereof, in which $R_1$, $R_2$, $R_3$, $R_4$, $R_5$, $R_7$, $R_8$, $R_9$, A, D, Z, X and Y are as defined above, (j) producing a compound of formula I in which $R_8$ and $R_9$ are both hydrogen, by selective hydrogenation of a corresponding compound of formula I in which $R_8$ and $R_9$ together form a single bond, or (k) producing a compound of formula I in which an adjacent pair of $R_1$, $R_2$, $R_3$ and $R_7$ represents hydroxy and alkanoyl C2 to 6, by selective ring opening of a corresponding compound of formula XXXII,

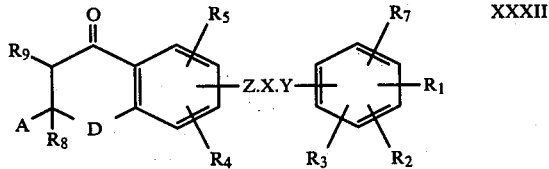

or a salt, ester or amide thereof, in which

A, D, $R_1$, $R_2$, $R_3$, $R_4$, $R_5$, $R_7$, $R_8$, $R_9$, X, Y and Z are as defined above, save that an adjacent pair of $R_1$, $R_2$, $R_3$ or $R_7$ represents the group —COC($R_{11}$)=C(-G)—O—, where $R_{11}$ represents alkyl, and G represents alkyl, phenyl, or carboxy.

In process (a) the group $D_1$ may be, for example, an alkoxy (C1 to 10) carbonyl group, a carboxamide group, a mono- or di- alkyl- (C1 to 10) carboxamido group, or an N-phenylcarboxamido group. The hydrolysis may be carried out using conventional techniques, for example under acidic or under alkaline conditions. The reaction may conveniently be carried out in a suitable aqueous solvent, for example an aqueous lower alkanol, at a temperature of from about 20° to 120° C.

In process (b)(i) the reaction may be carried out in the presence of a non-nucleophilic base, e.g. sodium hydride or methyl lithium. The reaction may be carried out in a solvent which is inert under the reaction conditions, for example benzene, dimethylformamide or dimethoxyethane. The reaction may be carried out at a temperature of from about 15° to 150° C.

In process (b)(ii) the reaction may be carried out in the presence of a basic catalyst and in a solvent (which when the solvent is basic may also act as catalyst) for example pyridine, or titanium tetrachloride. The reaction is preferably carried out at a temperature of from about 60° to 120° C.

In process (c), the reduction may be carried out using conventional techniques for the selective reduction of such compounds, e.g. catalytic hydrogenation in a suitable solvent, e.g. ethanol or acetic acid, at atmospheric pressure and using a palladium on charcoal or a palladium on barium sulphate catalyst (Lindlar's catalyst), at room temperature.

The reaction of process (d) may be carried out at a temperature of from about 200° to 300° C. The reaction is preferably carried out by simply heating the compound of formula II. $A_1$ may be, for example, phenyl or p-toluenesulphonyl.

The reaction of process (e) is conveniently effected by means of an alkali-metal hydroxide, e.g. sodium or potassium hydroxide, in a suitable solvent medium, e.g. water.

In process (f) salts may be prepared by treating a compound of formula I, an ester or an amide thereof, or another salt thereof with an appropriate base, e.g. an alkali-metal base, or with an appropriate salt by a metathetical process.

Esters may be made by treating a compound of formula I, or an amide or salt thereof, or another ester thereof with an appropriate alcohol, for example a C1–6 alkanol, e.g. ethyl or methyl, in the presence of an acid, e.g. sulphuric acid. Salts of compounds of formula I may be converted to C1–6 alkyl esters by reaction with the appropriate alkyl halide, e.g. ethyl iodide, methyl bromide, in a suitable solvent, e.g. dimethyl formamide, at about 20° to 40° C.

Amides may be made by treating an ester of a compound of formula I, for example a p-nitrophenol ester, with the appropriate amine, e.g. ammonia, methylamine, or aniline. Derivatives of the carboxy group of compounds of formula I, for example, the acid halide, e.g. chloride, the acid anhydride, the mixed acid anhydride, e.g. trifluorosulphonyl, may be treated with an appropriate amine, in the presence of a suitable base, e.g. triethylamine, or pyridine, in a suitable solvent, e.g. chloroform or dioxan, at ambient temperature.

In the reaction between compounds of formulae XX and XXI in process (g), when L or M is a reactive metal the metal may be, for example, an alkali-metal, e.g. sodium or another reactive metal, e.g. thallium. When L or M represents a hydrocarbon chain carrying a leaving group, the leaving group may be, for example, a halogen atom, e.g. bromine, or a sulphonate group, e.g. a methyl sulphonate or a p-toluenesulphonate group. When L or M represents a hydrocarbon chain carrying a halogen atom the reaction may be carried out in the presence of a solvent which is inert under the reaction conditions, e.g. acetone and in the presence of an acid acceptor, e.g. potassium carbonate. The reaction is also preferably carried out under anhydrous conditions and in the presence of a suitable catalyst, e.g. KI. When L or M represent a hydrocarbon group carrying an epoxide, the reaction may be carried out at an elevated temperature in a solvent which is inert under the reaction conditions, e.g. dioxan or dimethylformamide, and in the presence of a suitable catalyst, e.g. trimethylbenzylammonium hydroxide. Alternatively, the reaction may be carried out at an elevated temperature in a tertiary alcohol, e.g. t-butanol or 1,1-dimethylpropan-1-ol and in the presence of the potassium salt of the alcohol, or in the presence of an alkali-metal hydroxide in a suitable solvent, e.g. an alkanol such as ethanol.

The cyclisation of process (h) may conveniently be effected by means of an acid. The reaction may be effected by heating a solution of the compound of formula XXX in an appropriate solvent medium, e.g. an alkanol such as methanol, and by adding the appropriate acid. Desirably the acid is a hydrohalic acid, especially hydrochloric acid, and the reaction is effected by passing the gaseous hydrogen halide through the solution. Displaceable protecting groups that $Y_1$ may represent include alkyl, silyl or phenylalkyl, e.g. benzyl.

In process (i) the reaction may be carried out by heating to from about 200°–300° C., preferably under an inert atmosphere, e.g. nitrogen or by using the dehydrative environment provided by a strong acid, e.g. sulphuric or phosphoric acid, at ambient temperatures to 120° C.

In process (j) the hydrogenation is carried out by conventional techniques in an inert solvent, e.g. methanol, over a suitable catalyst, e.g. Raney nickel or palladium supported on carbon, at a temperature of from about 0°–50° C.

In process (k) the ring opening may be carried out using aqueous acid. However, basic hydrolysis conditions are preferred, using for example, a nucleophilic base, e.g. sodium hydroxide, in a suitable solvent, e.g. water, ethanol or dioxan, at a temperature of from about 20° to 120° C.

The compounds of formula I, and the intermediates therefor, may be recovered from their reaction mixtures by using conventional techniques.

The starting matarials of formula II for processes (a), (c) and (f) may be made by appropriate processes analogous to processes (b), (d) (e) or (j), or by converting, e.g. esterifying a corresponding compound of formula I.

The starting materials of formula II for process (b) are either known compounds or may be made from known compounds using appropriate processes analogous to process (g).

The starting materials of formula II for process (d) may be made by reacting a compound of the formula VII,

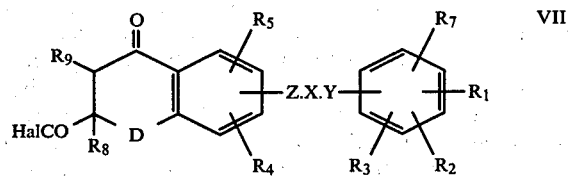

in which $R_1, R_2, R_3, R_4, R_5, R_7, R_8, R_9, D, Z, X$ and $Y$ are as defined above, and Hal represents halogen, e.g. chlorine, bromine, with a compound of the formula HOOC—CH=P(R)$_3$, or an ester thereof.

The starting materials of formula II for process (e) may be prepared by reacting a compound of formula VII with the anion of a dialkyl malonate, and heating the resulting product with an arene sulphonic anhydride, e.g. toluenesulphonic acid.

The compounds of formula XX and XXI may be made from known compounds using processes analogous to processes described above.

The compounds of formula XXX may be made by reacting a compound corresponding to formula XXX wherein $X_1$ is $R_9CH_2CO$ with a compound HOOCQCOE, or an ester thereof, where E is an anionic leaving group (e.g. halogen or alkoxy) in the presence of a suitable base and an inert solvent followed by cyclisation by a methods analogous to those described in process (h). The base may be, for example, sodium hydride, and suitable solvents include dioxan and dimethylformamide.

When G and A are the same, the compounds of formula XXXII may be made by reacting the corresponding compound of formula XXX where $X_1$ represents $R_9CH_2CO$ and an adjacent pair of $R_1, R_2, R_3$ and $R_7$ represent hydroxy and alkanoyl C2 to 6, as described immediately above.

The compounds of formula XXXII may also be made from known compounds by methods analogous to those described in process (g).

Other starting materials may be made from known compounds using conventional techniques known per se.

Some of the groups $R_1$ to $R_9$ and X may be affected by the reaction conditions described above. Where necessary or desirable, therefore, the reaction may be carried out using protected derivatives of the reagents.

The processes described above may produce the compound of formula I or a derivative thereof. It is also within the scope of this invention to treat any derivative so produced to liberate the free compound of formula I, or to convert one derivative into another.

Those compounds of formula I in which Q represents an alkenylene group may exist as cis or trans isomers.

Where one or more asymmetric carbon atoms are present the compounds may exist as optically active isomers or racemic or other mixtures thereof. Optically active compounds may be resolved using conventional techniques.

The compounds of formula I and their pharmaceutically acceptable derivatives possess pharmacological properties. In particular, they are antagonists of the slow reacting substance of anaphylaxis (SRS-A) or its pathological effects, as indicated by their activity in the test described by Augstein et al, Nature New Biology, 1973, 245, 215.

The compounds are thus indicated for use in the treatment of disorders in which SRS-A is a factor, for example skin afflictions, hay fever and obstructive airways diseases, e.g. asthma, bronchitis and bronchorrhea.

For the above mentioned uses, the dosage administered will, of course, vary depending upon the compound employed, mode of administration and treatment desired. However, in general satisfactory results are obtained when administered at a daily dosage of from about 0.05 milligrams to about 10 milligrams per kilogram of animal body weight, preferably given in divided doses 2 to 4 times a day or in sustained release form. For the larger mammals, the total daily dosage is in the range of from about 1 milligram to about 700 milligrams and dosage forms suitable for administration comprise from about 12 milligrams to about 350 milligrams of the compound admixed with a solid or liquid pharmaceutical carrier or diluent. The compounds may be administered during or before the attack of the disorder to be treated.

The compounds of formula I and the pharmaceutically acceptable derivatives thereof, are more active, more stable, more selective, less toxic or possess less side effects when tested in certain pharmacological models, are more potent, have a different (e.g. longer) duration of action, have a different absorption profile (e.g. are better absorbed), are more water soluble, are more easily formulated or possess other advantageous properties when compared to similar known compounds.

According to our invention we also provide a pharmaceutical composition comprising (preferably a minor proportion of) a compound of formula I, or a pharmaceutically acceptable salt, amide or ester thereof, in admixture with a pharmaceutically acceptable adjuvant, diluent or carrier. Examples of suitable adjuvants, diluents or carriers are:—for tablets and dragées; lactose, starch, talc or stearic acid; for capsules, tartic acid or lactose; for suppositories, natural or hardened oils or waxes; for inhalation a coarse carrier, e.g. lactose or a compressed gas propellant, e.g. a chlorofluorohydrocarbon, and optionally a surfactant; and for topical application, wool fat, soft paraffin or a cream BP. For use in such compositions, the compound of formula I, or the pharmaceutically acceptable salt, ester or amide thereof, preferably has a mass median diameter of from 0.01 to 10 microns. The compositions may also contain suitable preserving, stabilising and wetting agents, solubilizers, sweetening and colouring agents and flavourings. The compositions may, if desired, be formulated in sustained release form. We prefer compositions which are designed to be administered by inhalation.

For the above-mentioned uses, the dosage administered will, of course, vary depending upon the compound.

The invention is illustrated, but in no way limited by the following Examples. All temperatures are in °C.

EXAMPLE 1

Sodium 7-(3-[4-acetyl-3-hydroxy-2-propylphenoxy]-2-hydroxypropoxy)-2,3-dihydro-4-oxo-8-propyl-4H-1-benzopyran-2-carboxylate (a) Methyl 7-(3-[4-acetyl-3-hydroxy-2-propylphenoxy]-2-hydroxypropoxy)-2,3-dihydro-4-oxo-8-propyl-4H-1-benzopyran-2-carboxylate Methyl 7-(3-[4-acetyl-3-hydroxy-2-propylphenoxy]-2-hydroxypropoxy)-4-oxo-8-propyl-4H-1-benzopyran-2-carboxylate (4.0 g) in anhydrous methanol (400 ml) was hydrogenated at 45 p.s.i. over Raney nickel (about 1 ml of slurry) for 1.5 hours. The catalyst was filtered off and the residue was evaporated to a gum, which was chromatographed over silica gel with ether to afford the title ester as a solid (2.6 g).

Analysis Found: C, 65.1; H, 6.8%. $C_{28}H_{34}O_9$ Requires: C, 65.35; H, 6.7%.

(b) 7-[3-(4-Acetyl-3-hydroxy-2-propylphenoxy)-2-hydroxypropoxy]-2,3-dihydro-4-oxo-8-propyl-4H-1-benzopyran-2-carboxylic acid The product of step (a), (1.6 g) was refluxed with an excess of aqueous ethanolic sodium bicarbonate for 0.5 hours, cooled, acidified, and extracted with a mixture of ethylacetate and ether. Evaporation gave a gum which was dissolved with an equivalent of sodium bicarbonate in water, filtered, and acidified to afford the sub-title acid as a solid (1.4 g), mp 68°-72°.

(c) Sodium 7-(3-[4-acetyl-3-hydroxy-2-propylphenoxy]-2-hydroxypropoxy)-2,3-dihydro-4-oxo-8-propyl-4H-1-benzopyran-2-carboxylate The salt was prepared by dissolving the acid and an equivalent of sodium bicarbonate in water and freeze-drying the resulting solution.

Analysis: Found: C, 56.6; H, 6.2%. $C_{27}H_{31}NaO_9.3H_2O$ Requires: C, 56.2; H, 6.4%.

EXAMPLE 2

7-[3-(4-Acetyl-3-hydroxy-2-propylphenoxy)propoxy]-2,3-dihydro-4-oxo-8-propyl-4H-1-benzopyran-2-propanoic acid The title compound was prepared from appropriate starting materials, by processes analogous to those in Example 1, to give the title compound, mp 148°–150°, and its corresponding sodium salt.

EXAMPLE 3

7-(3-[4-Acetyl-3-hydroxy-2-propylphenylthio]-propyloxy)-4-oxo-8-propyl-4H-1-benzopyran-2-propanoic acid: L-lysine salt (a) Ethyl 7-(3-bromopropyloxy)-4-oxo-8-propyl-4H-1-benzopyran-2-propanoate Ethyl 7-hydroxy-4-oxo-8-propyl-4H-1-benzopyran-2-propanoate (9.12 g) suspended in acetone (200 ml) was added over 16 hours to a stirred, refluxing mixture of dibromopropane (60 g) and anhydrous potassium carbonate (4.2 g) in acetone (200 ml) containing potassium iodide (0.1 g). The mixture was refluxed for a further 16 hours, filtered while hot, and then the filtrate was evaporated, finally at 60° at 0.3 mm to leave a red oil, which was partitioned between water and ethyl acetate. The organic layer was washed with 5% sodium hydroxide solution, dried and evaporated to an oil, which was extracted repeatedly with hot light petroleum (bp 40°–60°). Evaporation of the extracts and crystallisation from cyclohexane gave the sub-title ester as needles (4.5 g), mp 78.5°–79°.

(b) Ethyl 7-(3-[4-acetyl-3-hydroxy-2-propylphenylthio]-propyloxy-4-oxo-8-propyl-4H-1-benzopyran-2-propanoate The product of step (a), (3.0 g), 2-hydroxy-4-mercapto-3-propylacetophenone (1.7 g) and anhydrous potassium carbonate (1.1 g) were stirred in acetone under nitrogen for 3 days. The mixture was poured into water, extracted with ethyl acetate and washed with 5% NaOH. Evaporation gave a red oil, which was chromatographed on silica gel with methylene chloride-ethyl acetate to give the sub-title ester (2.5 g), mp 89°–91°.

Analysis: Found: C, 67.4; H, 6.8; S, 5.9%. $C_{31}H_{38}O_7S$ Requires: C, 67.1; H, 6.9; S 5.8%.

(c) 7-(3-[4-Acetyl-3-hydroxy-2-propylphenylthio]-propyloxy)-4-oxo-8-propyl-4H-1-benzopyran-2-propanoic acid The product of step (b), (1.95 g) and an equivalent of sodium hydroxide in aqueous ethanol were stirred for 16 hours. Acidification gave a solid, which was crystallised from ethanol to yield the sub-title acid (0.95 g), mp 122°–124°.

Analysis: Found: C, 64.3; H, 6.7; S, 6.4%. $C_{29}H_{34}O_7S$ 0.75 $H_2O$ Requires: C, 64.5; H, 6.6; S, 5.9%.

(d)

7-(3-[4-Acetyl-3-hydroxy-2-propylphenylthio]-propyloxy)-4-oxo-8-propyl-4H-1-benzopyran-2-propanoic acid: L-lysine salt To the product of step (c) (0.75 g) dissolved in methanol was added L-lysine (0.21 g) in water. The solution was evaporated to remove the methanol, and the residual solution was freeze-dried to afford the title salt.

Analysis: Found: C, 59.2; N, 3.9; S, 4.5%. Thermogravimetric analysis (TGA) indicates 5.2% water. $C_{35}H_{48}N_2O_9S + 5.2\%$ water Requires C, 59.2; N, 4.0; S, 4.55%. After drying, Found: H, 7.15%. Requires: H, 7.2%.

EXAMPLE 4

7-[3-(4-Acetyl-3-amino-2-propylphenylthio)propoxy]-4-oxo-8-propyl-4H-1-benzopyran-2-propanoic acid The title compound was prepared from appropriate starting materials, by processes analogous to those in Example 3, mp 153°–155°, and its corresponding sodium salt.

Sodium salt analysis: Found: C, 58.85; H, 5.9; N, 2.3; S, 5.3%. $C_{29}H_{34}NNaO_6S.2.5H_2O$ Requires: C, 58.7; H, 6.6; N, 2.4; S, 5.4%.

EXAMPLE 5

Sodium 7-(3-[4-acetyl-3-hydroxy-2-propylphenoxy]-propoxy)-4-oxo-8-propyl-4H-1-benzothiopyran-2-carboxylate (a) Methyl 7-(3-[4-acetyl-3-hydroxy-2-propylphenoxy)-propoxy)-4-oxo-8-propyl-4H-1-benzothiopyran-2-carboxylate Methyl 7-hydroxy-4-oxo-8-propyl-4H-1-benzothiopyran-2-carboxylate (1 g) and 4-(3-bromopropoxy)-2-hydroxy-3-propylacetophenone (2 g) and anhydrous potassium carbonate (0.5 g) in dimethylformamide (20 ml) were stirred for 16 hours under nitrogren, poured into water, and extracted with ethyl acetate, which was washed with water, dried, and evaporated to a solid. Chromatography on silica gel with petroleum ether (bp 40°–60°): ethyl acetate (2:1) gave the sub-title ester (1.36 g), mp 130°–131°.

(b) 7-(3-[4-Acetyl-3-hydroxy-2-propylphenoxy]propoxy)-4-oxo-8-propyl-4H-1-benzothiopyran-2-carboxylic acid The ester from step (a) was hydrolysed by the process described in Example 1 (b) to give the sub-title acid, mp 177°–178°. Analysis: $C_{27}H_{30}O_7S$ Requires: C, 65.1; H, 6.0; S, 6.4%. Found: C, 64.8; H, 6.1; S, 6.4%.

(c) Sodium 7-(3-[4-acetyl-3-hydroxy-2-propylphenoxy]-propoxy)-4-oxo-8-propyl-4H-1-benzothiopyran-2-carboxylate The acid from step (b) was converted to the title salt by the process of Example 1(c).

Analysis: Found: C, 57.0; S, 5.25%. Karl Fischer water determination shows 8.33% water. $C_{27}H_{29}NaO_7S + 8.33 H_2O$ Requires: C, 57.1; S, 5.6%. After drying, Found: H, 5.2%. Requires: H, 5.6%.

EXAMPLE 6

The following acids, and their corresponding sodium salts, were prepared from appropriate starting materials, by processes analogous to those in Example 5:

(i) 7-(3-[4-Acetyl-3-hydroxy-2-propylphenoxy]propoxy)-1,4-dihydro-4-oxo-8-propylquinoline-2-propanoic acid, mp 188°–189°, (Ethyl ester 91°–92°).

(ii) 7-(3-[4-Acetyl-3-hydroxy-2-propylphenoxy]propoxy)-4-oxo-6-propyl-4H-1-benzothiopyran-2-carboxylic acid, mp 193°–196° (Methyl ester, mp 128°–130°), Sodium salt analysis: Found: C, 55.4; H, 5.0; S, 6.8%. TGA 4.9% $H_2O$. $C_{22}H_{29}NaO_7S + 4.9\% H_2O$ Requires: C, 55.2; H, 5.0; S, 6.5%.

(iii) 7-(3-[4-Acetyl-3-hydroxy-2-propylphenoxy]-propoxy)-4-oxo-8-propyl-4H-1-benzothiopyran-2-propenoic acid; (Ethyl ester, mp 161°–163°), (iv) 7-(5-[2-Acetyl-3-hydroxyphenoxy)pentyloxy]-4-oxo-8-propyl-4H-1-benzothiopyran-2-carboxylic acid.

EXAMPLE 7

Sodium 7-(3-(4-acetyl-3-hydroxy-2-propylphenoxy)-2-hydroxypropoxy]-4-oxo-8-propyl-4H-1-benzothiopyran-2-carboxylate Methyl 7-hydroxy-4-oxo-8-propyl-4H-1-benzothiopyran-2-carboxylate (1 g), 4-(2,3-epoxypropoxy)-2-hydroxy-3-propylacetophenone (2.25 g), and sodium hydroxide (0.16 g) in ethanol (50 ml) were refluxed for 6 hours. Further quantities of the acetophenone (1.1 g) and sodium hydroxide (0.08 g) were added, and the mixture was refluxed for a further 5 hours. The solvent was evaporated and the residue was dissolved in water and washed with ethyl acetate. The aqueous layer was acidified to give a gum, which after chromatography on silica gel with methylene chloride:methanol (5:1) gave 7-[3-(4-acetyl-3-hydroxy-2-propylphenoxy)- 2-hydroxypropoxy]-4-oxo-8-propyl-4H-1-benzothiopyran-2-carboxylic acid (1 g), mp 280°–281°.

The title sodium salt was prepared by the method of Example 1(c).

EXAMPLE 8

The following acids, and their corresponding sodium salts, were prepared from appropriate starting materials by processes analogous to those in Example 7:

(i) 7-[3-(4-Acetyl-3-hydroxy-2-propylphenoxy)-2-hydroxypropoxy]-4-oxo-6-propyl-4H-1-benzothiopyran-2-carboxylic acid, mp 176°–178° (Methyl ester, mp 134°–137°).

Sodium salt analysis: Found: C, 55.3; H, 4.6; S, 5.2%. TGA 8.5% $H_2O$. $C_{27}H_{29}NaO_8S + 8.5\% H_2O$ Requires: C, 55.3; H, 5.0; S, 5.5%.

(ii) 7-[3-(4-Acetyl-3-hydroxy-2-propylphenoxy)-2-hydroxypropoxy]-1,4-dihydro-4-oxo-8-propylquinoline-2-propanoic acid, glass, $^1H$ NMR (DMSO-d6): δ 12.7(1H,s); 8.23(1H,d,J=9.5 Hz); 7.62 (1H,d,J=9.0 Hz); 7.10(1H,d,J=9.5 Hz); 6.55(1H,d,J=9.0 Hz); 6.40(1H,s); 4.34(6H,m); 2.8(8H,m); 2.60(3H,s); 1.5(4H,m); 0.95(6H,m). (Ethyl ester, mp 75°–78°).

EXAMPLE 9

Sodium 7-[3-(2-acetyl-3-hydroxyphenoxy)-2-hydroxypropoxy]-1,4-dihydro-4-oxoquinoline-2-carboxylate (a) 2-[3-(3-Nitrophenyloxy)-2-hydroxypropoxy]-6-hydroxyacetophenone To 3-nitrophenol (8.7 g) and 2-(2,3-epoxypropoxy)-6-hydroxyacetophenone (13 g) in ethanol (150 ml) was added a solution of sodium hydroxide (0.25 g) in ethanol (25 ml), and the mixture was refluxed for 16 hours. The solvent was evaporated and the residue was treated with water to give the sub-title compound, (19 g), mp 125°–132° (from ethanol).

(b) 2-[3-(3-Aminophenyloxy)-2-hydroxypropoxy]-6-hydroxyacetophenone

A suspension of the product from step (a) (15 g) in ethanol (100 ml) was hydrogenated at atmospheric pressure over 5% palladium on charcoal. Evaporation of the solvent and trituration of the residue with petroleum ether (bp 40°–60°) gave the sub-title compound, (11 g), mp 108°–111°.

(c) Methyl 7-[3-(2-Acetyl-3-hydroxyphenoxy)-2-hydroxypropoxy]-1,4-dihydro-4-oxo-quinoline-2-carboxylate The product from step (b) (11.0 g) and dimethyl acetylenedicarboxylate (50 g) in methanol (250 ml) were refluxed for 5 minutes. The solvent was evaporated and the residue was chromatographed on silica gel with petroleum ether (bp 40°–60°): ether (3:1) to give dimethyl (3-[3-(2-acetyl-3-hydroxyphenoxy)-2-hydroxypropyloxy] phenylamino)butenedioate (10.3 g) as an oil. The oil was added to refluxing diphenyl ether (250 ml). After 3 minutes the solution was added to an excess of petroleum ether (bp 40°–60°) to give a yellow solid, which was collected, triturated with ether, and then chromatographed on silica gel with chloroform:methanol (9:1) to furnish the sub-title compound (3.3 g), mp 192°–194°, characterised by $^1$H NMR.

Analysis: Found: C, 61.3; H, 5.0; N, 3.1%. $C_{22}H_{21}NO_8$ Requires: C, 61.8; H, 4.9; N, 3.3%.

(d) Sodium 7-[3-(2-acetyl-3-hydroxyphenoxy)-2-hydroxypropoxy)-1,4-dihydro-4-oxoquinoline-2-carboxylate To the ester from step (c) (1.06 g) in refluxing methanol was added dropwise 0.1 N sodium hydroxide (25 ml). The solvent was evaporated and the residue was dissolved in water and freeze-dried to afford the title salt $^1$H NMR (DMSO-d6): δ 8.06(IH,d, J=9.5 Hz); 7.52(IH,broad s); 7.41(IH,t,J=8 Hz); 7.01(IH,dd, J=2.5 Hz; 9.5 Hz); 6.66(IH,d,J=8 Hz); 6.61(IH,s); 6.57(IH,d,J=8); 4.25(6H, broad s); 2.64(3H,s)

EXAMPLE 10

Sodium 7-[3-(4-acetyl-3-hydroxy-2-propylphenoxy)propylthio]-1,4-dihydro-4-oxo-8-propylquinoline-2-carboxylate

(a) Ethyl 7-[3-(2-ethoxycarbonyl-4-oxo-8-propyl-4H-1-benzopyran-7-yloxy)propylthio]-1,4-dihydro-4-oxo-8-propyl-quinoline-2-carboxylate 4-[3-(4-Acetyl-3-amino-2-propylphenylthio)propoxy]-2-hydroxy-3-propylacetophenone (14 g) in ethanol (200 ml) was added to a solution of sodium (6.5 g) in ethanol (350 ml) at 40°. Diethyl oxalate was added slowly and the stirred mixture was heated at 65°–70° for two hours. The mixture was poured into water, acidified to pH 5, and extracted with ethyl acetate, which was dried and evaporated to an oil. The oil was dissolved in dry dioxan (150 ml) which was then saturated with dry hydrogen chloride, and the mixture was heated to 70° for 1.5 hours. The mixture was diluted with water and extracted with ethyl acetate, which was washed well with water, dried and evaporated to a gum. Trituration with petroleum ether (bp 40°–60°) and chromatography of the residue on silica gel with methylene chloride:ethyl acetate (7.3) gave, after crystallisation from ethanol, the sub-title diester (3.4 g), mp 168°–170°.

Analysis: Found: C, 65.0; H, 6.1; N, 2.25; S, 5.4%. $C_{33}H_{37}NO_8S$ Requires: C, 65.2, H, 6.1, N, 2.3, S, 5.3%.

(b) Sodium 7-[3-(4-acetyl-3-hydroxy-2-propylphenoxy)-propylthio]-1,4-dihydro-4-oxo-8-propylquinoline-2-carboxylate The diester from step (a) (0.2 g) was refluxed in ethanol (10 ml) containing N sodium hydroxide solution (1.0 ml) for two hours. The solution was poured into brine and extracted with ethyl acetate. The organic phase was shaken with a little dilute hydrochloric acid, separated, and evaporated to give a solid, which, after crystallisation from ethanol, afforded 7-[3-(4-acetyl-3-hydroxy-2-propylphenoxy)propylthio]-1,4-dihydro-4-oxo-8-propylquinoline-2-carboxylic acid (0.085 g), mp 192°–194°.

Analysis: Found: C,64.0; H, 6.8; N, 2.5; S, 6.2%. $C_{27}H_{31}NO_6S \cdot C_2H_5OH$ Requires: C,64.1; H, 6.9; N, 2.6; S, 5.9%.

This acid was converted to the title sodium salt by the method of example 1(c).

Sodium salt analysis: Found: C, 59.1; N, 2.5; S, 5.8%. $C_{27}H_{30}NNaO_6S \cdot 1.5H_2O$ Requires: C, 59.3; N, 2.6; S, 5.85%. After drying, Found: H, 5.3%. Requires: H, 5.8%.

EXAMPLE 11

By processes analogous to those described in Example 10, using appropriate starting materials the following intermediates were prepared and hydrolysed to give the following acids and their sodium salts.

(i) Ethyl 7-[3-(2-ethoxycarbonyl-4-oxo-8-propyl-4H-1-benzopyran-2-yloxy)propoxy]-1-ethyl-1,4-dihydro-4-oxo-6-propylquinoline-2-carboxylate (solid, characterised by $^1$H NMR and mass spectroscopy) was hydrolysed to give 7-(3-[4-acetyl-3-hydroxy-2-propylphenyloxy]propoxy)-1-ethyl-1,4-dihydro-4-oxo-6-propylquinoline-2-carboxylic acid, mp 194°–195° (decomp).

(ii) Ethyl 7-[3-(2-ethoxycarbonyl-4-oxo-8-propyl-4H-1-benzopyran-2-yloxy)propoxy]-1,4-dihydro-4-oxo-8-propylquinoline-2-carboxylate, mp 137°–138°, was hydrolysed to give 7-[3-(4-acetyl-3-hydroxy-2-propylphenoxy)propoxy]-1,4-dihydro-4-oxo-8-propylquinoline-2-carboxylic acid, mp 215°–217° (decomp).

Sodium salt analysis: Found: C, 60.65; H, 5.8; N, 2.6%. $C_{27}N_{30}NNaO_7 \cdot 1.75H_2O$ Requires: C, 60.6; H, 6.3; N, 2.6%.

(iii) Ethyl 7-[3-(2-ethoxycarbonyl-4-oxo-8-propyl-4H-1-benzopyran-2-yloxy)-2-hydroxypropoxy]-1,4-dihydro-4-oxo-8-propylquinoline-2-carboxylate, mp 107°–109°, was hydrolysed to give 7-[3-(4-acetyl-3-hydroxy-2-propylphenoxy)-2-hydroxypropoxy]-1,4-dihydro-4-oxo-8-propylquinoline-2-carboxylic acid, mp 212°–214° (decomp).

Sodium salt analysis: Found: C, 58.4; H, 5.5; N, 2.5%. $C_{27}N_{30}NNaO_8 \cdot 2H_2O$ Requires: C, 58.4; H, 6.2; N, 2.5%.

(iv) Ethyl 7-[3-(2-ethoxycarbonyl-4-oxo-8-propyl-4H-1-benzopyran-2-yloxy)propoxy]-1,4-dihydro-4-oxo-6- proylquinoline-2-carboxylate (solid, characterised by ¹H NMR and mass spectroscopy) was hydrolysed to give 7-[3-(4-acetyl-3-hydroxy-2-propylphenoxy)-propoxy]-1,4-dihydro-4-oxo-6-propylquinoline-2-carboxylic acid, mp 251°–252° (decomp).

(v) Ethyl 7-[3-(2-ethoxycarbonyl-4-oxo-6,8-dipropyl-4H-1-benzopyran-2-yloxy)propoxy]-1,4-dihydro-4-oxo-8-propylquinoline-2-carboxylate, mp 128°–131° was hydrolysed to give 7-[3-(4-acetyl-3-hydroxy-2,6-dipropylphenoxy)propoxy]-1,4-dihydro-4-oxo-6-propylquinoline-2-carboxylic acid, mp 145°–148°.

EXAMPLE 12

Sodium 7-[3-(4-acetyl-3-amino-2-propylphenylthio)propoxy]-4-oxo-8-propyl-4H-1-benzopyran-2-carboxylate (a) Ethyl 7-[3-(4-acetyl-3-amino-2-propylphenylthio)propoxy]-4-oxo-8-propyl-4H-1-benzopyran-2-carboxylate 4-[3-(4-Acetyl-3-amino-2-propylphenylthio)propoxy]-2-hydroxy-3-propylacetophenone (3.1 g) in ethanol (50 ml) was added to a solution of sodium (0.6 g) in ethanol (100 ml) at 45°. After 30 minutes diethyl oxalate (2.1 g) was added and the mixture was stirred for 2.5 hours. The mixture was poured into dilute hydrochloric acid and extracted with ethyl acetate, which was dried and evaporated to an oil. The oil was refluxed in ethanol previously saturated with hydrogen chloride. The solvents were removed and the residue was chromatographed on silica gel with methylene chloride:ethyl acetate (95:5) to give, after crystallisation from ethanol, the sub-title ester (0.6 g), mp 103°–104°.

(b) Sodium 7-[3-(4-acetyl-3-amino-2-propylphenylthio)propoxy]-4-oxo-8-propyl-4H-1-benzopyran-2-carboxylate The ester from step (a) (0.5 g) was hydrolysed by the method of Example 1 (b) to give 7-[3-(4-acetyl-3-amino-2-propylphenylthio)propoxy]-4-oxo-8-propyl-4H-1-benzopyran-2-carboxylic acid (0.4 g), mp 202°–204°.

Analysis: Found: C, 65.2; H, 6.3; N, 2.7; S, 6.8%. C$_{27}$H$_{31}$NO$_6$S Requires: C, 65.1; H, 6.3; N, 2.8; S, 6.4%.

This acid was converted to the title sodium salt by the method of Example 1(c).

Sodium salt analysis: Found: C, 59.5; H, 5.8; N, 2.45; S, 6.0%. C$_{27}$N$_{30}$NNaO$_6$.1.5H$_2$O Requires: C, 59.3; H, 6.1; N, 2.5; S, 5.8%.

Preparation of Novel Intermediates

A. (a) 4-(3-[4-acetyl-3-amino-2-propylphenoxy]propoxy)-2-hydroxy-3-propylacetophenone 2-amino-4-hydroxy-3-propylacetophenone (3.9 g), 4-(3-bromopropoxy)-2-hydroxy-3-propylacetophenone (6.3 g), potassium carbonate (3.1 g) and a crystal of potassium iodide were stirred in dry dimethyl formamide at 50° under nitrogen for 2 days. The mixture was poured into dilute hydrochloric acid and extracted with ethyl acetate, which was washed with water, dried and evaporated to an oil. Chromatography on silica gel with dichloromethane: ethyl acetate (97:3) gave the title compound as a clear oil (7 g), characterised by ¹H NMR and mass spectroscopy.

(b) By a similar process 2,4-dihydroxy-3-propylacetophenone and 2-amino-4-(3-bromopropylthio)-3-propylacetophenone gave 4-(3-[4-acetyl-3-amino-2-propylphenylthio]propoxy)-2-hydroxy-3-propylacetophenone, mp 93°–95°.

(c) Similarly 2-amino-4-hydroxy-5-propylacetophenone and 4-(3-bromopropoxy)-2-hydroxy-3-propylacetophenone gave 4-(3-[4-acetyl-3-amino-5-propylphenoxy]propoxy)-2-hydroxy-3-propylacetophenone, mp 103°–105°.

(d) Similarly 2-amino-4-hydroxy-3-propylacetophenone and 4-(3-bromopropoxy)-2-hydroxy-3,5-dipropylacetophenone gave 4-(3-[4-acetyl-3-amino-2-propylphenoxy]propoxy)-2-hydroxy-3,5-dipropylacetophenone, mp 84°–86°.

B. 4-(3-[4-Acetyl-3-amino-2-propylphenoxy]-2-hydroxypropoxy)-2-hydroxy-3-propylacetophenone 2-Amino-4-hydroxy-3-propylacetophenone (5.85 g), 4-(2,3-epoxypropoxy)-2-hydroxy-3-propylacetophenone (11.25 g), and benzyltrimethylammonium hydroxide (5 drops of 40% aqueous solution) in dimethylformamide (100 ml) were heated at 130° under nitrogen for 5 hours. The mixture was poured into 2% hydrochloric acid and extracted with ethyl acetate, which was washed with water, dried and evaporated to give the title compound as an oil (14.3 g), characterised by ¹H NMR and mass spectroscopy.

C. 4-(3-[4-Acetyl-3-ethylamino-6-propylphenoxy]propoxy)-2-hydroxy-3-propylacetophenone A solution of 4-(3-[4-acetyl-3-amino-5-propylphenoxy]propoxy)-2-hydroxy-3-propylacetophenone (2.45 g) in ethanol (50 ml) and acetaldehyde (15 ml) was cooled to −5° and 5% palladium on charcoal (0.5 g) was added. The mixture was stirred at room temperature under hydrogen at atmospheric pressure for 15 hours. The mixture was filtered, and the filtrate was evaporated to an oil which was chromatographed on silica gel with dichloromethane to give the title compound as an oil (1.1 g), characterised by ¹H NMR and mass spectroscopy.

D. Methyl 7-hydroxy-4-oxo-6-propyl-4H-1-benzothiopyran-2-carboxylate (a) O-[3-hydroxy-4-(1-oxopropyl)phenyl]-N,N-dimethylthiocarbamate Dimethylthiocarbamoylchloride (62 g) in acetone (200 ml) was added slowly to 2,4-dihydroxypropiophenone (66 g), potassium carbonate (62 g) and acetone (500 ml) stirred at room temperature. After a further 16 hours at room temperature and 2 hours at reflux, the cooled mixture was filtered and the solvent was removed. The residue was recrystallised from ethyl acetate-petroleum ether to give the sub-title compound (72 g), mp 137°–139°.

The following were prepared by a similar method using appropriate starting materials:
O-(4-Acetyl-3-amino-2-propylphenyl)-N,N-dimethylthiocarbamate, mp 123°–125°.
O-(4-Methyl-2-oxo-8-propyl-2H-1-benzopyran-7-yl)-N,N-dimethylthiocarbamate, mp 143.5°–144.5°.

(b)
S-[3-Hydroxy-4-(1-oxopropyl)phenyl]-N,N-dimethylcarbamothioate

O-[3-Hydroxy-4-(1-oxopropyl)phenyl]-N,N-dimethylthiocarbamate (64 g) was heated at 220° for 2 hours under nitrogen and cooled to room temperature. The crude product was recrystallised from aqueous ethanol to give the sub-title compound (62 g), mp 76°–77°.

The following were prepared by a similar method:
S-(4-acetyl-3-amino-2-propylphenyl)-N,N-dimethylcarbamothioate, mp 123°–126°.
S-(4-Methyl-2-oxo-8-propyl-2H-1-benzopyran-7-yl)-N,N-dimethylcarbamothioate, mp 120°–121°.

(c)
S-[3-hydroxy-4-propylphenyl]-N,N-dimethylcarbamothioate

S-[3-Hydroxy-4-(1-oxopropyl)phenyl]-N,N-dimethylcarbamothioate (38 g) in toluene (80 ml) was added to zinc amalgam (49 g) in 20% aqueous hydrochloric acid (120 ml) and a stream of HCl gas was passed through the mixture, which was heated to reflux for 3 hours. The cool mixture was filtered and extracted with ether. The combined ether layers were washed with dilute aqueous sodium bicarbonate solution, and water, and dried. Solvent was removed to give an orange solid. This was recrystallised from ether: petroleum ether to give the sub-title compound (24 g), mp 99°–103°.

(d) 3-hydroxy-4-propylbenzenethiol

The product from step (c) (48 g), potassium hydroxide (67 g), ethanol (200 ml) and water (300 ml) were heated at reflux for 18 hours. The cool solution was poured into water and the aqueous phase was washed with ether, adjusted to pH 3–4 with hydrochloric acid and extracted with ethyl acetate. The combined extracts were washed with brine and dried. Solvent was removed and the residue was distilled to give the sub-title compound as a colourless oil (26 g), bp 112°–116° (0.05 mm).

By a similar method and using appropriate starting materials the following were prepared:
2-Amino-4-mercapto-3-propylacetophenone (oil).
3-Mercapto-2-propylphenol, bp 80°–84° (0.02 mm).

(e) Methyl 7-hydroxy-4-oxo-6-propyl-4H-1-benzothiopyran-2-carboxylate

3-Hydroxy-4-propylbenzenethiol (26 g) was dissolved in water (450 ml) containing potassium hydroxide (25 g). Solid acetylene dicarboxylic acid mono potassium salt (23 g) was then added and the mixture was heated at 50° for one hour. The cool solution was poured into water and the aqueous solution was washed with dichloromethane, adjusted to pH 2–3 with hydrochloric acid and extracted with ethyl acetate. The combined extracts were washed with brine, dried and evaporated to give an oil which was redissolved in dichloromethane:petroleum ether. On cooling a pale yellow solid was obtained (23 g), which was added portion-wise to chlorosulphonic acid (60 ml) stirred efficiently at 5°. After 2 minutes the resulting viscous oil was added dropwise to crushed ice and the resulting aqueous mixture was extracted with ethyl acetate whilst cold. The combined extracts were washed with water, dried and evaporated to give a residue, which was suspended in methanol, saturated with hydrogen chloride (200 ml), and then heated at gentle reflux for 36 hours. The solution was cooled and the precipitate was collected and recrystallised from ethyl acetate to give the sub-title compound (11.5 g), mp 260°–262° (dec).

Analysis: $C_{14}H_{14}O_4S$ Requires: C, 60.4; H, 5.1; S, 11.5. Found: C, 60.4; H, 5.1; S, 11.3%.

By a similar method methyl 7-hydroxy-4-oxo-8-propyl-4H-1-benzothiopyran-2-carboxylate, mp 259°–260°, was prepared.

E. 2-Amino-4-hydroxy-5-propylacetophenone (a) N-(2-Acetyl-5-allyloxyphenyl)acetamide N-(2-Acetyl-5-hydroxyphenyl)acetamide (1.93 g), potassium carbonate (1.4 g) and allyl bromide (1 ml) were refluxed in dry acetone (60 ml) for 16 hours. Water was added and the mixture was extracted with ethylacetate, which was washed with 5% sodium hydroxide solution, and water, dried and evaporated to give the sub-title compound (1.2 g), mp 63°–64° (from cyclohexane).

(b) N-(2-acetyl-4-allyl-5-hydroxyphenyl)acetamide

The product from step (a) (0.20 g) and N-methylpyrrolidone (5 ml) were refluxed for 8 hours under nitrogen. The mixture was poured into water and extracted with ethyl acetate, which was in turn extracted with 5% sodium hydroxide solution. Acidification of the basic layer gave the sub-title compound (0.1 g), mp 172°–174°.

(c) 2-Amino-4-hydroxy-5-propylacetophenone

The product from step (b) (1 g) was refluxed with ethanol (10 ml) and concentrated hydrochloric acid (10 ml) for 15 minutes, poured into water, and extracted with ethyl acetate, which was then washed with water, dried and evaporated. The residue was dissolved in ethanol (50 ml) and hydrogenated at atmospheric pressure over 10% palladium on charcoal. Evaporation of the solvent afforded the title compound, characterised by $^1$H NMR and mass spectroscopy.

F. Ethyl 1,4-dihydro-7-hydroxy-4-oxo-8-propylquinoline-2-propanoate (a) Ethyl 7-benzyloxy-1,4-dihydro-4-oxo-8-propylquinoline-2-carboxylate 2-Amino-4-hydroxy-3-propylacetophenone (10.7 g), benzyl chloride (8 g), potassium carbonate (8.37 g) and potassium iodide (0.2 g) in dry acetone (250 ml) were stirred at 60° for 16 hours. The mixture was filtered, and the filtrate was evaporated to an oil, which after chromatography on silica with methylene chloride gave 2-amino-4-benzyloxy-3-propylacetophenone (8.3 g), characterised by $^1$H NMR. This compound (6 g) in ethanol was added to a solution of sodium (4.9 g) in ethanol (150 ml). Diethyl oxalate (15.6 g) was added and the mixture was stirred at 70° for 2 hours, poured into water and extracted with ethyl acetate. Evaporation of the organic phase gave a residue which was dissolved in dry dioxan and treated with hydrogen chloride. The mixture was heated at 60° for 2 hours, poured into water and extracted with ethyl acetate, which on evaporation, and chromatography (silica gel, ethylacetate:methylene chloride 1:4) of the subsequent residue, gave the sub-title compound, mp 121°–122°.

(b)
7-Benzyloxy-2-formyl-1,4-dihydro-8-propylquinoline-4-one

The product from step (a) (1.0 g) in dry ethanol at 0° was stirred under nitrogen and treated with sodium borohydride (0.83 g). The mixture was allowed to warm to room temperature over one hour, poured into water and extracted with ethyl acetate. Evaporation of the solvent gave 7-benzyloxy-1,4-dihydro-2-hydroxymethyl-8-propylquinoline-4-one (0.8 g), mp 197°–199°. This alcohol (5.5 g) was refluxed in dry chloroform (100 ml) with manganese dioxide (5.5 g) for 22 hours, and then filtered. The filtrate was chromatographed (silica gel, ethyl acetate:methylene chloride 1:1) to give the sub-title compound (3.7 g), mp 162°–163°.

By an analogous process using appropriate starting materials, 7-hydroxy-2-hydroxymethyl-8-propyl-4H-1-benzothiopyran-4-one (characterised by $^1$H NMR and mass spectroscopy) was prepared, and converted to 2-formyl-7-hydroxy-8-propyl-4H-1-benzothiopyran-4-one, mp 209°–212°.

(c) Ethyl 3-[7-benzyloxy-1,4-dihydro-4-oxo-8-propylquinoline-2-yl]propenoate

Sodium hydride (0.075 g) was added to triethylphosphonoacetate (0.7 g) in dry dimethyl formamide (25 ml) under nitrogen. The reaction mixture was then maintained at 35° for 30 minutes.

7-Benzyloxy-2-formyl-1,4-dihydro-8-propylquinoline-4-one (0.5 g) in dimethyl formamide (10 ml) was added. After 30 minutes at 35° the mixture was poured into dilute hydrochloric acid and extracted with ethyl acetate. Evaporation of the solvent gave the sub-title compound (0.36 g), characterised by $^1$H NMR and mass spectroscopy.

By a similar process and using appropriate starting materials ethyl 3-[7-hydroxy-4-oxo-8-propyl-4H-1-benzothiopyran-2-yl]propenoate, mp 221°–223°, was prepared.

(d) Ethyl 1,4-dihydro-7-hydroxy-4-oxo-8-propylquinoline-2-propanoate

Ethyl 3-[7-benzyloxy-1,4-dihydro-4-oxo-8-propylquinoline-2-yl]propenoate (2.35 g) in ethanol was hydrogenated at atmospheric pressure over 10% palladium on charcoal Removal of the solvent gave the title compound (2.4 g), characterised by $^1$H NMR and mass spectroscopy.

I claim:
1. A compound of formula I, in which
$R_1$, $R_2$, $R_3$, $R_4$, $R_5$ and $R_7$, which may be the same or different, each represent hydrogen, hydroxy, alkyl C1 to 6, alkoxy C1 to 6, amino, aklanoyl C2 to 6, alkanoylamino C2 to 6, alkenyl C2 to 6, halogen, or alkoxy C1 to 6 substituted by phenyl, X is a hydrocarbon chain of 1 to 10 carbon atoms unsubstituted or substituted by a single hydroxy group,
A is —Q—COOH,
Q is absent or represents a straight or branched alkylene, alkenylene or alkynylene group of up to and including 6 carbon atoms,
$R_8$ and $R_9$, which may be the same or different, each represent hydrogen or alkyl C1 to 6 or together form a single bond,
D is —$NR_{10}$—,
Y and Z, which may be the same or different, each represent sulphur, oxygen or —$NR_{10}$—, and
$R_{10}$ is hydrogen or alkyl C1–C6,
and pharmaceutically acceptable salts, esters and amides thereof.

2. A compound according to claim 1, wherein $R_1$, $R_2$, $R_3$, $R_4$, $R_5$ and $R_7$, which may be the same or different, each represent hydrogen, hydroxy, alkyl C1 to 6, amino or alkanoyl C2 to 6.

3. A compound according to claim 2, wherein Z and Y each represent oxygen.

4. A compound according to claim 3, wherein $R_8$ and $R_9$ together form a single bond.

5. A compound according to claim 4, wherein $R_1$ is in the 4-position with respect to Y, and represents hydrogen or alkanoyl of 2 to 4 carbon atoms, $R_2$ is in the 3-position with respect to Y and represents hydrogen, amino or hydroxy, $R_3$ is in the 2-position with respect to Y, and represents hydrogen, alkyl of 1 to 4 carbon atoms, or alkanoyl of 2 to 4 carbon atoms, $R_4$ is in the 8-position, and represents hydrogen or alkyl of 1 to 4 carbon atoms, $R_5$ is in the 6 position, and represents hydrogen or alkyl of 1 to 4 carbon atoms, $R_7$ is in the 6 position with respect to Y and represents hydrogen or alkyl 1 to 4 carbon atoms, Z is in the 7 position and represents oxygen, Y represents oxygen, X represents a straight chain alkylene of 3 to 5 carbon atoms unsubstituted or substituted by a single hydroxy group, and Q represents a straight chain alkylene or alkenylene group of 2 to 4 carbon atoms, and the pharmaceutically acceptable salts thereof.

6. A compound of formula I as defined in claim 1, which is
7-[3-(4-acetyl-3-hydroxy-2-propylphenoxy)-2-hydroxypropoxy]-1,4-dihydro-4-oxo-8-propylquinoline-2-carboxylic acid,
7-[3-(4-acetyl-3-hydroxy-2,6-dipropylphenoxy)propoxy]-1,4-dihydro-4-oxo-6-propylquinoline-2-carboxylic acid,
or a pharmaceutically acceptable salt thereof.

7. A compound of formula I, as defined in claim 1, which is
7-(3-[4-acetyl-3-hydroxy-2-propylphenoxy]propoxy)-1,4-dihydro-4-oxo-8-propylquinoline-2-propanoic acid,
7-[3-(4-acetyl-3-hydroxy-2-propylphenoxy)-propylthio]-1,4-dihydro-4-oxo-8-propylquinoline-2-carboxylic acid,
7-[3-(4-acetyl-3-hydroxy-2-propylphenyloxy)propoxy]-1-ethyl-1,4-dihydro-4-oxo-6-propylquinoline-2-carboxylic acid,
7-[3-(4-acetyl-3-hydroxy-2-propylphenoxy)propoxyl]-1,4-dihydro-4-oxo-8-propylquinoline-2-carboxylic acid,
7-[3-(4-acetyl-3-hydroxy-2-propylphenoxy)propoxy]-1,4-dihydro-4-oxo-6-propylquinoline-2-carboxylic acid, 7-[3-(4-acetyl-3-hydroxy-2-propylphenoxy)-2-hydroxypropoxy]-1,4-dihydro-4-oxo-8-propylquinoline-2-propanoic acid, 7-3-(2-acetyl-3-hydroxyphenoxy)-2-hydroxy-propoxy]-1,4-dihydro-4-oxoquinoline-2-carboxylic acid, 7-[3-(4-acetyl-3-hydroxy-2-propylphenoxy]propyloxy-1-ethyl-1,4-dihydro-4-oxo-8-propylquinoline-2-carboxylic acid, or a pharmaceutically acceptable salt thereof.

8. A pharmaceutical composition which comprises an effective amount of at least one compound according to claim 1, in association with a pharmaceutically acceptable adjuvant, diluent or carrier.

9. A method of treatment of a disorder in which SRS-A is a factor, which comprises administration of an effective amount of a compound according to claim 1 to a patient suffering from such a condition.

* * * * *